US010133852B2

(12) United States Patent
Lyakhov et al.

(10) Patent No.: US 10,133,852 B2
(45) Date of Patent: Nov. 20, 2018

(54) METHOD AND APPARATUS FOR CRYSTAL STRUCTURE OPTIMIZATION

(71) Applicant: The Research Foundation for The State University of New York, Albany, NY (US)

(72) Inventors: Andriy O. Lyakhov, Stony Brook, NY (US); Artem R. Oganov, Stony Brook, NY (US); Qiang Zhu, Stony Brook, NY (US)

(73) Assignee: The Research Foundation of The State University of New York, Albany, NY (US)

( * ) Notice: Subject to any disclaimer, the term of this patent is extended or adjusted under 35 U.S.C. 154(b) by 1023 days.

(21) Appl. No.: 14/404,994

(22) PCT Filed: Jun. 24, 2013

(86) PCT No.: PCT/US2013/047303
§ 371 (c)(1),
(2) Date: Dec. 2, 2014

(87) PCT Pub. No.: WO2014/004370
PCT Pub. Date: Jan. 3, 2014

(65) Prior Publication Data
US 2015/0127307 A1  May 7, 2015

Related U.S. Application Data

(60) Provisional application No. 61/663,828, filed on Jun. 25, 2012.

(51) Int. Cl.
*G06F 17/10* (2006.01)
*G06F 19/00* (2018.01)

(52) U.S. Cl.
CPC ................... *G06F 19/704* (2013.01)

(58) Field of Classification Search
CPC .................................................. G06F 17/5018
(Continued)

(56) References Cited

U.S. PATENT DOCUMENTS

2007/0185695 A1*  8/2007  Neumann ............. G06F 19/704
                                                            703/2
2009/0210366 A1   8/2009  Sakata et al.
2010/0023473 A1   1/2010  Neumann

FOREIGN PATENT DOCUMENTS

EP            1000347       12/2002
WO         WO 9906824        2/1999
WO       WO 2007071095       6/2007

OTHER PUBLICATIONS

Xingtao, Keyan Li et al., Electronegativity Identification of Novel Superhard Materials, Physical Review Letters 100, 235504 (2008), The American Physical Society, (pp. 4).
(Continued)

*Primary Examiner* — Andy Ho
(74) *Attorney, Agent, or Firm* — The Farrell Law Firm, P.C.; John F. Gallagher, III

(57) ABSTRACT

Disclosed is a method and system for prediction of an optimized crystal structure using an evolutionary algorithm that includes inputting characterization information of a chemical structure and input parameters, generating a first generation of crystal structures from the characterization information using symmetrical initialization, optimizing the chemical structure of the first generation of crystal structures according to the input parameters, inputting the optimized first generation of crystal structures into a niching algorithm, producing a child group of crystal structures from the parent group of crystal structures using a variation operator, and adding the child group of crystal structures to an optimal group of crystal structures to form a next generation, with the niching algorithm selecting an optimal group of crystal (Continued)

structures and a parent group of crystal structures from the first generation of crystal structures, with an antiseed created for population diversity and every structure produced by the evolutionary algorithm being stored together with a width and a height of the Gaussian parameter as the antiseed.

9 Claims, 5 Drawing Sheets

(58) Field of Classification Search
USPC .................................................. 703/2
See application file for complete search history.

(56) References Cited

OTHER PUBLICATIONS

Simunek, Antonin et al., Hardness of Covalent and Ionic Crystals: First-Principle . . . , Physical Review Letters 96, 085501 (2006), The American Physical Society, (pp. 4).

Gao, Faming et al., Hardness of Covalent Crystals, Physical Review Letters, vol. 91, No. 1, 2003, The American Phyiscal Society, (pp. 4).

Matsumoto, Makoto et al., Mersenne Twister: A 623-Dimensionally Equidistributed Uniform Pseudo-Random Number Generator, ACM . . . , vol. 8, No. 1, Jan. 1998, pp. 3-30.

Morris et al. ("Automated Docking Using a Lamarckian Genetic Algorithm and an Empirical Binding Free Energy Function", Journal of Computational Chemistry, 1998).

Oganov et al. (Crystal structure prediction using ab initio evolutionary techniques: Principles and applications, The Journal of Chemical Physics, 2006).

Motherwell et al. (Crystal structure prediction of small organic molecules: a second blind test, International Union of Crystallography, 2002).

Woodley et al. (Crystal structure prediction from first principles, Macmillan Publishers Limited, 2008).

PCT/ISA/237 Written Opinion issued on PCT/US2013/047303 (pp. 4).

* cited by examiner

METHOD AND APPARATUS FOR CRYSTAL STRUCTURE OPTIMIZATION

PRIORITY

This application claims priority to U.S. Provisional Patent Application No. 61/663,828 filed with the U.S. Patent and Trademark Office on Jun. 25, 2012, the content of which is incorporated herein by reference.

BACKGROUND OF THE INVENTION

1. Field of the Invention

The present invention relates generally to material design and, more particularly, to a method and apparatus using an evolutionary algorithm for to optimize crystal structure, including use of metadynamics to avoid the genetic drift.

2. Description of the Related Art

Evolutionary algorithms are widely used in the field of crystal structure prediction. Specifically, evolutionary algorithms are useful to determine a ground state of a crystal structure for a given chemical composition at given pressure and temperature conditions. The ground state refers to the crystal structure with a lowest possible free energy, i.e. enthalpy, for the chemical composition. An evolutionary algorithm of Universal Structure Predictor: Evolutionary Xtallography (USPEX) provides an efficient and reliable method and system for crystal structure prediction, improvements to which are disclosed herein.

USPEX is utilized in various applications, for example prediction of hardness, which is an important property for determination of new materials for applications such as cutting and drilling tools. The ability to predict a hardest phase of a crystal and other structures, for a given stoichiometry, enables a systematic search for novel hard materials and allows efficient evaluation of potentially controversial experimental results. Problems encountered utilizing conventional systems are summarized in *Modern Methods of Crystal Structure Prediction*, Andriy O. Lyakhov, et al., Wiley VCH (2011). Problems that arise in conventional systems include finding a global minimum on a surface in multidimensional space, such as hardness and free energy, as a function of the atomic positions and lattice vectors, respectively. Computing the hardness of a given crystal structure is a difficult task. Only recently has significant progress been achieved in formulating models that are physically meaningful and sufficiently accurate for several classes of compounds. See, F. Gao et al., Phys. Rev. Lett. 91, 0155021 (2003); A. Simunek et al., Phys. Rev. Lett. 96, 0855011 (2006); K. Li, et al., Phys. Rev. Lett. 100, 235504 (2008); and A. R. Oganov and A. O. Lyakhov, J. Superhard Mater. 32, 143 (2010).

Evolutionary crystal structure prediction begins with a set or population of crystal structures and evolves this set of crystal structures based on input parameters and variation operators that provide the conditions for optimization of the set of crystal structures to produce child crystal structures from parent crystal structures. A conventional method to determine next generations of crystal structures is provided in International Publication No. WO2007/071095 of Glass, et al. Child, i.e., next generation, crystal structures retain vestiges of parent crystal structures after operation of the variation operators, while new features are introduced into the child crystal structures. These new features include both desirable and undesirable characteristics. Variation operators include a heredity operator, which creates a child crystal structure from two or more parents, and a mutation operator, which creates a child using a single parent.

An initial population may be randomly created or input based on desired ground state information, such as likely candidate structures, lattice parameters, and space groups. Conventional evolutionary algorithms locally optimize the crystal structures, typically by relaxation of chemical bonds by a user determined theory, such as empirical potentials, density functional theory, hybrid functions and Quantum Monte Carlo algorithms.

However, conventional evolutionary algorithms generate crystal structures that often become trapped in a local free energy minimum rather than a global free energy minimum. In addition, a number of local minima rises exponentially as the crystal structure's size increases, further raising the risk of trapping. Accordingly, current evolutionary algorithms are limited to crystal structure prediction of materials of only 15-40 atoms in size.

Moreover, random input of conventional systems will often create an initial population of crystal structures that is randomly produced. Such random initialization typically leads to highly disordered output of nearly identical child structures with similar high energies and a low degree of order. Thus, conventional methods and systems fail to provide a method for optimized prediction of crystal structures, particularly for materials with larger sized molecules.

SUMMARY OF THE INVENTION

Accordingly, aspects of the present invention address the above problems and disadvantages and provide the advantages described below. An aspect of the present invention provides a method and system for prediction of an optimized crystal structure using an evolutionary algorithm that includes inputting characterization information of a chemical structure and input parameters, generating a first generation of crystal structures from the characterization information using symmetrical initialization, optimizing the chemical structure of the first generation of crystal structures according to the input parameters, inputting the optimized first generation of crystal structures into a niching algorithm, producing a child group of crystal structures from the parent group of crystal structures using a variation operator, and adding the child group of crystal structures to an optimal group of crystal structures to form a next generation, with the niching algorithm selecting an optimal group of crystal structures and a parent group of crystal structures from the first generation of crystal structures, with an antiseed created for population diversity and every structure produced by the evolutionary algorithm being stored together with a width and a height of the Gaussian parameter as the antiseed.

BRIEF DESCRIPTION OF THE DRAWINGS

The above and other aspects, features and advantages of certain embodiments of the present invention will be more apparent from the following detailed description taken in conjunction with the accompanying drawings, in which.

DETAILED DESCRIPTION OF EMBODIMENTS OF THE INVENTION

The following detailed description of certain embodiments of the present invention will be made with reference to the accompanying drawings. In describing the invention, explanation about related functions or constructions known in the art are omitted for the sake of clearness in understanding the concept of the invention, to avoid obscuring the invention with unnecessary detail.

Figure 1:
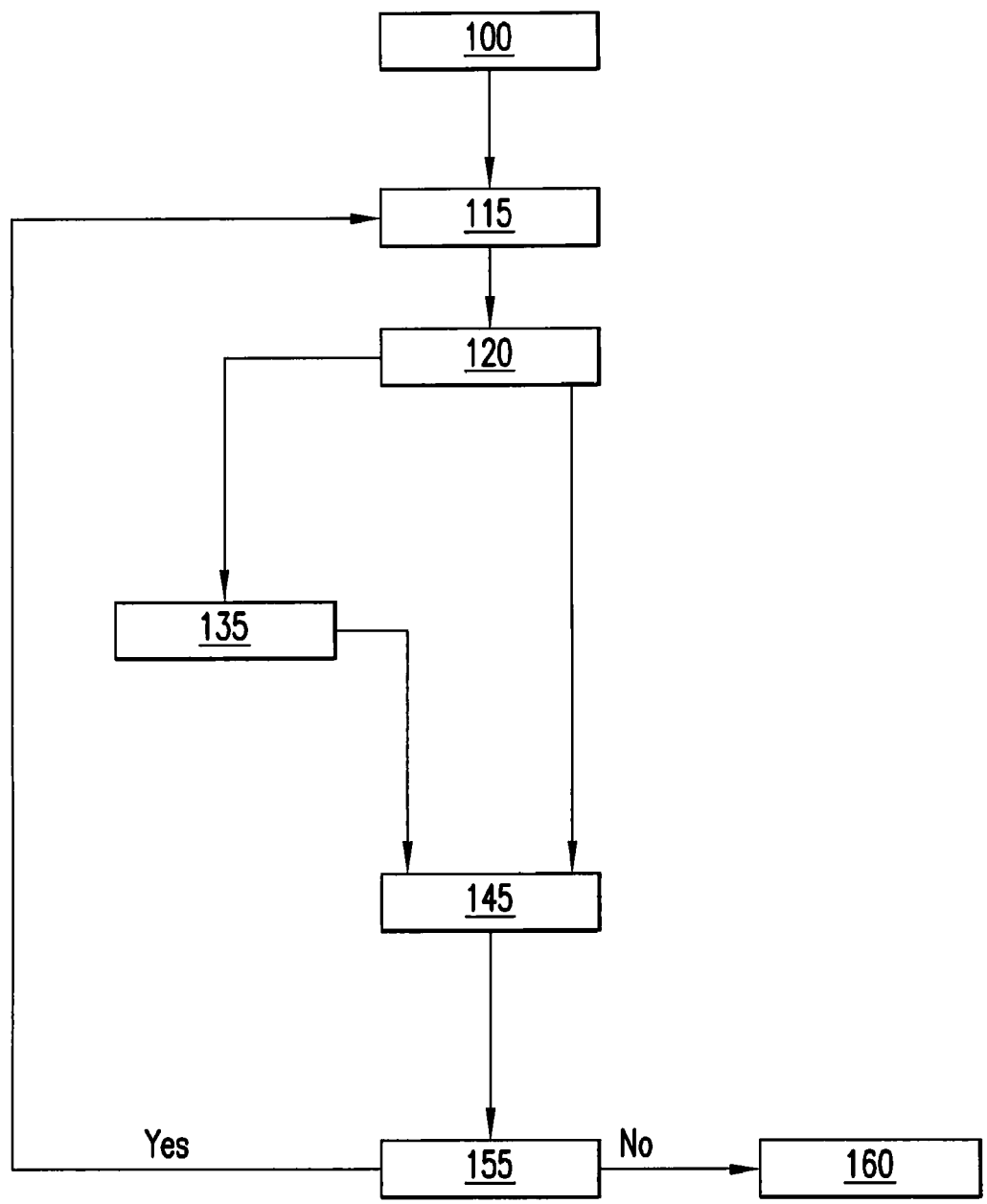
FIG. 1 is a flow chart of a method to predict optimized crystal structure using an evolutionary algorithm.

FIG. 1 illustrates a method for predicting an optimized crystal structure using an evolutionary algorithm. At step 100, characterization information of a chemical structure is input. The characterization information includes chemical formulas, an atomic number of an atom, a number of atoms in a unit cell, valences of atoms, and unit cell volume. The characterization information may also include known lattice parameters.

Following the inputting of characterization information, a first generation of crystal structures is obtained, preferably by a random input, seed input or symmetrical initialization. The first generation of crystal structures is described herein as being generated using a symmetrical initialization algorithm based on the input characterization information. A randomly produced crystal structure can be utilized to commence generation of crystal structures in step 115, with the symmetrical initialization algorithm randomly selecting a space group compatible with the number of atoms in a unit cell of the chemical structure. For example, the space group can be randomly selected from space groups using a Mersenne Twister algorithm. See, Matsumoto, M., et al., *Mersenne Twister: A 623-dimensionally Equidistributed Uniform Pseudo-Random Number Generator*, ACM Transactions on Modelling and Computer Simulation, 8 (1) (1998), pp. 3-30. The space group can also be randomly selected by a random number generator algorithm. The symmetrical initialization selects from either an entire list of two hundred and thirty space groups or selects from a user-provided list of space groups. A symmetrical initialization unit cell is then configured based on the selected space group and a predetermined initial volume.

The symmetrical initialization preferably includes adding symmetrical random structures in each generation to improve population diversity and provide new crystal structures to be explored by the evolutionary algorithm. The symmetrical initialization includes unit cell splitting to provide a reduced number of degrees of freedom of the crystal structures. The symmetrical initialization introduces additional translational symmetry, i.e., pseudosymmetry, to the crystal structures. The symmetrical initialization uses up to two hundred and thirty space groups, allowing the user to produce a diverse first generation of crystal structures.

Figure 2:
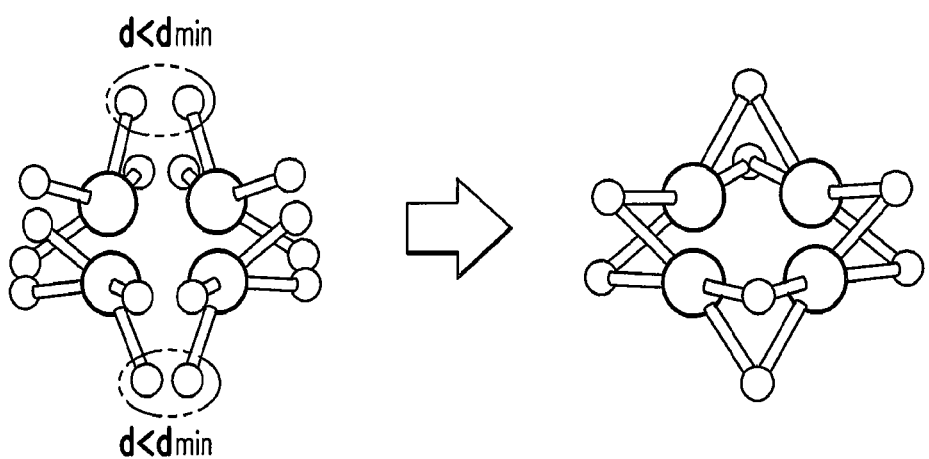
FIG. 2 illustrates atoms merging by coordinate averaging.

FIG. 2 illustrates merging of atoms based on determined averages of coordinates of each atom when a distance (d) between atoms for atomic pairs is smaller than a user determined threshold ($d_{min}$). Merging the atoms by averaging the coordinates is equivalent to merging the atoms on symmetry elements that were used to produce the atoms.

Using the symmetrical initialization algorithm, a plurality of atoms are randomly placed on separate first Wyckoff positions, herein a first position, and coordinates of each of the atoms are multiplied by space group symmetry operations. The first position of each of the atoms includes all points of a space group for which site-symmetry groups are conjugate subgroups of the space group. If an inter-atomic distance of two or more symmetry-related atoms is within a user-defined threshold, the symmetry-related atoms are merged into one atom on a second position defined by averaging of coordinates of symmetry-related atoms.

A sum of the merged atoms and remaining atoms outside of the user-defined threshold for the inter-atomic distance is compatible with the space group symmetry operation. However, discarding the merged atoms from a crystal structure of the first generation of crystal structures may be necessary if the sum is incompatible with the space group symmetry operation. New atoms are added one at a time to ensure that no atoms, including symmetrically unrelated atoms, are too closely positioned.

To obtain an exact number of atoms necessary in a unit cell, certain atoms are placed on special Wyckoff positions having a predetermined multiplicity. The multiplicity of the Wyckoff position refers to a number of atoms obtained after multiplying the atom in the Wyckoff position using a group symmetry element. For example, if six atoms are needed to reach the number of atoms in the unit cell, atoms are input into positions with multiplicities of one through six, but not with a multiplicity larger than six. Otherwise after multiplication, more atoms than are desired for the unit cell are obtained. This process of symmetrical initialization provides an unbiased procedure for sampling of each allowed space group and placing of atoms in positions that ensure distances of at least $d_{min}$ between all atoms. If symmetrically related atoms are closer than the user-defined threshold, they are merged into the second position, as illustrated by FIG. 2. If symmetrically non-equivalent atoms are within a user-defined threshold for distance between atoms, the crystal structure is discarded without relaxation. The user-defined threshold is one of the user input parameters, which in a preferred embodiment is set to a half sum of the covalent radii of the corresponding atoms.

Returning to step 115 of FIG. 1, local optimization of the chemical structure of the first generation of crystal structures according to the input parameters occurs. Local optimization, i.e., relaxation, does not break individual cell symmetry, but increases symmetry of the entire supergroup. Preferably, random displacement of atomic positions provides a possibility of breaking symmetry. Variation operators are also provided to break symmetry, and to remove bias that may have been caused by the selected space group.

After optimization, in step 120 the optimized first generation of crystal structures is input into a niching algorithm to select two separate groups of crystal structures from the optimized first generation of crystal structures. The niching algorithm calculates a set of conventional fitness functions and a set of fingerprint functions for each crystal structure of the first generation of crystal structures. The set of fitness functions allows the user to assess the quality of the crystal structures in the first generation of crystal structures according to a chemical property of the chemical structure to be optimized. The chemical property includes free energy, density, hardness, dielectric constant and bandgap. The set of fingerprint functions allows the user to assess the similarity between each of the crystal structures of an optimal group of crystal structures and the parent group of crystal structures.

A fingerprint function of a crystal structure is calculated according to Equation (1):

$$F_{A_iB}(R) = \sum_{B_j} \frac{\delta(R - R_{ij})}{4\pi R_{ij}^2 N_B \Delta}, \quad (1)$$

where $N_B$ is a number of type B atoms in the unit cell, $R_{ij}$ is inter-atomic distance between atoms $A_i$ and $B_j$, $\delta(R-R_{ij})$ is a Gaussian-smeared delta function, which absorbs numerical errors and makes F(R) a smooth function. Gaussian smearing is controlled by an input parameter sigmaFing. F(R) is discretized over bins of width $\Delta$ to obtain a fingerprint vector $FP_{A_iB}$. Bins of width $\Delta$ are preferably specified by the user as an input parameter.

The fingerprint function of Equation (1) is provided for individual type $A_i$ atoms relative to all $B_j$ type atoms, with $B_j$ type atoms surrounding atom $A_i$ with a sum running over all $B_j$ atoms within a distance threshold $R_{max}$, which preferably is user specified as an input parameter RmaxFing, with $R_{max}$ referring to a sum over all atoms $B_j$ for which $R_{ij}<R_{max}$.

The niching algorithm includes determining a degree of similarity between a plurality of fingerprint functions from the set of fingerprint functions. Specifically, to determine a degree of similarity between crystal structures of $A_i$ and $B_j$ type atoms, a cosine distance $d_{ij}$ between fingerprint functions $FP_i$ and $FP_j$ of crystal structures $A_i$ and $B_j$, respectively, is calculated according to Equation (2):

$$d_{ij} = 0.5\left(1 - \frac{FP_i FP_j}{\|FP_i\|\|FP_j\|}\right), \quad (2)$$

where $FP_i$ is a fingerprint vector of crystal structure of $A_i$, $\|FP_i\|$ is a norm of the $FP_i$ fingerprint vector, $FP_j$ is a fingerprint vector of crystal structure of $B_j$, and $\|FP_j\|$ is a norm of a $FP_j$ fingerprint vector, which is a result of discretization of the fingerprint function calculated according to Equation (1).

In Equation (2), the set of fingerprint functions, and thus the associated crystal structures, are considered identical if $d_{ij}$ is less than a distance threshold input by the user. For example, when $d_{ij}$ is smaller than 0.005, the crystal structures are considered identical. Where identical structures are determined, only those having a best fitness function, i.e., structures having a lowest free energy, are selected to create child crystal structures. Since pairs of parent crystal structures cannot be fully identical, the diversity of the next population improves by employing the niching algorithm.

In a preferred embodiment, step 120 further includes determining a value of the fitness function for each crystal structure of the first generation of crystal structures from a set of fitness functions. An optimal group of crystal structures is selected according to the value of the fitness function and a degree of similarity. The optimal group of crystal structures may be selected according to a user-defined threshold for the fitness function. For example, crystal structures having a free energy below the user-defined threshold are included in the optimal group of crystal structures. Alternatively, the user-defined threshold may define the optimal group of crystal structures as a percentage, such that the crystal structures having a top 20% fitness function value are included in the optimal group of crystal structures.

To improve diversity when selecting the optimal group of crystal structures, a first optimal crystal structure from the parent group of crystal structures is discarded when a distance between the fingerprint function of the first optimal crystal structure and the fingerprint function of a second optimal crystal structure is smaller than a user-defined distance threshold, wherein fingerprint distance is a metric for an energy landscape.

The parent group of crystal structures is also selected according to the value of the fitness function. The parent group of crystal structures may be selected according to a user-defined threshold for free energy. For example, crystal structures having a free energy above the user-defined threshold for the optimal group of crystal structures are included in the parent group of crystal structures. Alternatively, the user-defined threshold may define the optimal group of crystal structures as a percentage, such that the crystal structures within the remaining 80% of fitness function values are included in the optimal group of crystal structures. However, the user-defined thresholds for the optimal group of crystal structures and the parent group of crystal structures may overlap.

To improve diversity when selecting the parent group of crystal structures, a first parent crystal structure from the parent group of crystal structures is discarded when a distance between the fingerprint function of the first parent crystal structure and the fingerprint function of a second parent crystal structure is smaller than the user-defined threshold. The user-defined threshold for the distance between the fingerprint functions of the parent group of crystal structures is input as input parameter preferably as a 10% increase in strictness to require more diverse crystal structures.

Output of the niching algorithm of step 120 of FIG. 1 provides an optimal group of crystal structures that survive unchanged into a next generation. The optimal group of crystal structures is selected as the first selected group, which represents crystal structures having most desirable crystal structures, i.e. structures with lowest free energy, from the optimized first generation of crystal structures.

In a preferred embodiment, a metadynamics method is provided for sampling the energy landscape. The metadynamics method utilizes a form of conformational flooding, to add Gaussian potentials to the real energy landscape of the system at all sampled points. See, Grubmüller, H., Phys. Rev. E 52, p 2893 (1995). The metadynamics method discourages revisiting of already-sampled regions of the search space, to explore other regions of the landscape. In a preferred aspect, every structure produced by USPEX is stored together with two parameters: the width and the height of the Gaussian parameter. These structures are referred to as antiseeds. The Gaussian parameters evolve with time and depend on the diversity of the population at the moment of antiseed creation. To create an additional evolutionary pressure on already sampled structures, the fitness of a structure i is modified using Equation (3):

$$f_i = f_{i0} + \sum_a W_a \exp\left(-\frac{D_{ia}^2}{2\sigma_a^2}\right), \quad (3)$$

where $f_{i0}$ is an initial fitness function, e.g., energy, summation is performed over each stored antiseed having height $W_a$ and width $\sigma_a$, $D_{ia}$ is a distance between a current structure and an antiseed structure in a fingerprint metric space, $\sigma_a$ is proportional to the average cosine distance between fingerprints of all pairs of structures in a population, e.g., 0.05<d>, and $W_a$ is proportional to a fitness variance, e.g., 0.01σ(E).

Antiseeds enhance algorithm success rate, particularly for systems with complex multifunnel energy landscapes. Modification of fitness function of Eq. (3) introduces ageing (and, eventually, death) of individuals in the evolutionary process. As an alternative to ageing via antiseeds, direct ageing of surviving structures can be introduced by lowering respectively probability of selection as parents for each generational survival. Results of antiseed application for different crystalline structures are provided in Table 1.

TABLE 1

| System (number of atoms/cell) | Anti-seeds | Symmetric initialization | Success rate (%) | Average number of structures until global minimum is found | Dispersion |
|---|---|---|---|---|---|
| SrTiO$_3$ | – | – | 94 | 524 | 297 |
| TiO$_2$ (48) | – | – | 100 | 41 | 40 |
| SiO$_2$-coesite (48) | + | + | 100 | 591 | 537 |
| Mg$_2$Al$_{16}$Si$_{24}$O$_{96}$ (160) | + | + | 100 | 296 | 327 |

Tables 1-2 provide parameters of evolutionary runs and results of use of antiseeds with the USPEX algorithm for a range of systems.

TABLE 2

|  | SrTiO$_3$ | TiO$_2$ | SiO$_2$ | Mg$_{24}$Al$_{16}$Si$_{24}$O$_{96}$ |
|---|---|---|---|---|
| Population size | 25 | 10 | 40 | 40 |
| Max. Number of generations | 40 | 40 | 60 | 30 |
| Number of calculations | 35 | 73 | 68 | 64 |
| % of structures generated by: |  |  |  |  |
| Heredity | 40% | 50% | 30% | 30% |
| Softmutation | 20% | 20% | 30% | 30% |
| Permutation | 20% | 10% | 10% | 10% |
| Lattice mutation | 20% | 20% | 0% | 0% |
| Symmetric random | 0% | 0% | 30% | 30% |

The central test case of Lonie and Zurek, Comput. Phys. Comm, 182 pp. 2305-2306 (2001), claimed a success rate of 7%-12% as being good for a SrTiO3 system of 50 atoms in the cell. The performance of USPEX was tested by performing thirty-five calculations with the same interatomic potential model and limiting the number of generations to forty and the size of the generation to twenty-five structures, to replicate the one-thousand structure searches from Lonie and Zurek. The success rate was 94%, which increased to 100% when calculations were extended to 70 generations. The average number of structures required to obtain the global minimum was just 524. The ground state with this model has five atoms in the unit cell, without use of antiseeds or space group initialization. Softmutation was used and the initial generation was produced by the cell splitting technique with split-factors of two and four.

The other system tested in Lonie and Zurek was titania (TiO2) with 48 atoms in the cell. A comparative test of a preferred embodiment used the same potential as used in Lonie and Zurek. The ground state is the rutile structure, which contains six atoms in the unit cell. For this system seventy-three calculations were performed and a 100% success rate was obtained. The average number of structures required to obtain the ground state is 41. In this calculation, antiseeds and space group initialization were not used. Cell splitting (split-factors 2 and 4) for the first generation and softmutation were used.

Figure 3:
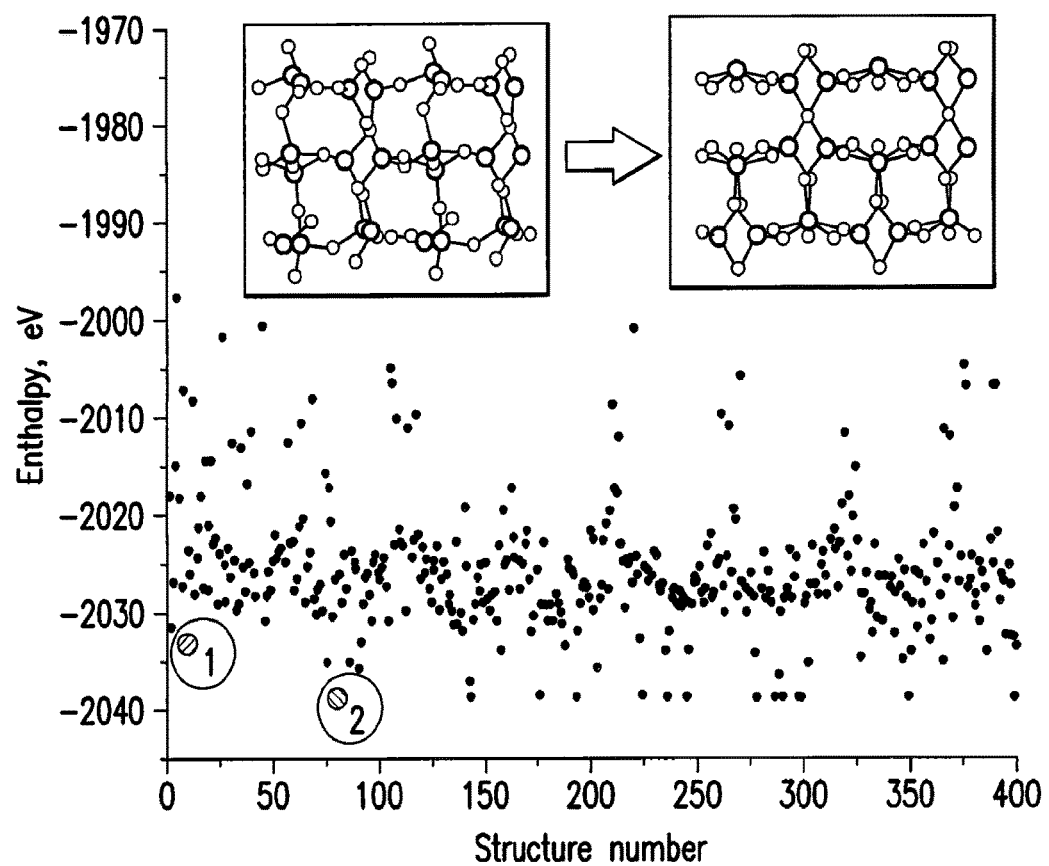
FIG. 3 is a graph illustrating optimized crystal structure predictions for coesite at a fixed unit cell, according to an aspect of the present invention.

USPEX was also tested on coesite, a polymorph of SiO2 with 48 atoms in the conventional cell. This calculation used the relatively crude fully ionic potential model with conventional shell model and parameters. See, Catlow, C. R. A., Proc. R. Soc. Lond. Ser. A 353 pp. 533-561 (1977), Sanders, M. J. et al., J. Cem. Soc. Chem. Commun. 19, pp. 1271 (1984), and Gavezzotti, A. Chem. Res. 27, pp. 309-314 (1995). As a constraint, the experimental unit cell parameters were used, with a 100% success rate, often obtaining the structure in a few generations, as shown in FIG. 3. An example of an empirically obtained first threshold is provided in FIG. 3, which provides results for calculations for coesite at fixed unit cell. As shown in FIG. 3, structure 2 was obtained from structure 1 by softmutation.

The parent group of crystal structures selected in step 120 of FIG. 1 is output from the optimized first generation of crystal structures according to the fitness function. The parent group of crystal structures selected from the optimized first generation of crystal structures are chosen as a user defined function of the optimal group of crystal structures.

Thereafter, in step 135, a child group of crystal structures are produced from the parent group of crystal structures using a variation operator that includes one of a lattice mutation operator, a coordinate mutation operator, a spatial heredity operator and an atomic permutation operator, to produce a child group of crystal structures from the parent group of crystal structures according to user-defined proportions. For example, 25% of the parent group of crystal structures will be input into each of the lattice mutation operator, the coordinate mutation operator, the spatial heredity operator, and the atomic permutation operator to produce the child group of crystal structures.

Random variation operators provide a diverse population by exploring an entire search space. Randomness ensures an unbiased search and limits genetic drift. However, completely random variation operators are typically inefficient when applied to crystal structures with a unit cell size of over forty atoms. To improve the variation operators, a local order element is introduced. For individual atoms i=[1, ... , N] in the unit cell, the local order element is calculated using the crystal structure's fingerprint function, with the local order element for atom i determined according to Equation (4):

$$\prod_i = \sqrt{\sum_B \frac{N_B}{N} \frac{\Delta}{(V/N)^{1/3}} |F_{A_i B}|^2}, \quad (4)$$

where i=[1, ... , N] denoting individual atoms in a unit cell, N is a total number of atoms in the unit cell, V is a unit cell volume, $FP_{A_i B}$ is a fingerprint vector of $A_i$, and B represents all atom types present in the unit cell. $\Pi_i$ is a local order element for atom i and $\Pi_i$ characterizes environment quality and atomic position symmetry, with a smaller value of $\Pi_i$ for a given atom indicating a larger probability that the given atom will mutate.

In step 135 of FIG. 1, the local order element quantifies a degree of symmetry of the environment of a given atom and also quantifies the average degree of order of a fragment of a crystal structure. Thus, the less distorted and less defective regions of the crystal structure may be input into the spatial heredity operator and more defective regions of the crystal structures may be input into the lattice mutation operator and the atomic permutation operator. When the local order element is low, a number of defects and distortion are high. Where the local order element is high, the number of defects and distortion are low. However, a value of the local order element depends on factors that include atoms involved and atomic positions. If distortions or defects are favorable, the user may select those regions of the crystal structures accordingly.

Also in step 135, a plurality of slices are selected from a parent group of crystal structures in a spatial heredity operator as a function of an order-fitness function correlation coefficient according to an aspect of the present invention. Each slice is a portion of a crystal structure formed when the crystal structure is cut along two parallel planes. All atoms located between these planes form the slice. Specifically, two parallel cuts are made through the crystal structures and the portion of crystal structure between the parallel cuts is the slice. The spatial heredity operator preferably includes generating a number of slices of a unit cell and selects a slice from slices having a highest average order. Specifically, in the spatial heredity operator, the slices of the unit cell are selected from a plurality of crystal structures from the parent group of crystal structures and the slices are then combined to produce the child group of crystal structures. The slices selected from the parent group of crystal structures in the spatial heredity operator function as an order-fitness correlation coefficient. To improve diversity of crystal structures, a user may incorporate portions of both the less distorted and defective regions, as well as the more distorted and defective regions. To determine which portions to incorporate, correlation between the average order of the crystal structures and the fitness value of the crystal structures is calculated. Depending on the degree of correlation, the degree to which the local order element influences the variation operators is determined. When there is a positive correlation, $N_s$ attempts to cut the slices are made from each parent and the most ordered slices are selected. That is, the number of slices of the unit cell from which the slice with the highest average order is selected is determined according to Equation (5):

$$N_s = \frac{L}{L_{char} + (L - L_{char}) \cdot \cos(\frac{\pi}{2}r)^2}, \qquad (5)$$

where $N_s$ is the number of slices, $r \in [-1;1]$ is a Pearson product-moment correlation coefficient, L is a thickness of a unit cell in a direction of the slice for the spatial heredity operator, and $L_{char}$ is a length of half of a cubic root of an average atomic volume, with $N_s$ rounded to the nearest integer. Thus, $N_s$ changes from a value of one in the absence of correlation (r=0) to $L/L_{char}$ for perfect correlation.

According to an aspect of the present invention, the coordinate mutation operator preferably includes mutating atoms with lower order, and displaces each atom in the unit cell in a random direction. A degree of displacement is inversely proportional to the local order $\Pi_i$ of the atom.

Also in step 135, the variation operator includes a soft mode mutation operator, according to an aspect of the present invention. Using the soft mode mutation operator, atoms are moved along eigenvectors of softest modes, since low-frequency eigenmodes imply low curvature of an energy surface and likely also low energy barriers. The softest modes refer to modes with smallest eigenfrequencies. Specifically, the soft mode mutation operator includes diagonalising a dynamical matrix to obtain eigenfrequencies and eigenvectors, though the atoms need not move exactly along the eigenvector. To overcome an energy barrier and end up in a new free energy minimum, an approximate direction and sufficiently large mutation amplitude is provided to arrive at a new low-energy minimum. The soft mode mutation operator also includes selecting a lowest non-zero eigenfrequency and moving atoms along a corresponding eigenvector and setting an amplitude of displacement.

Since the user does not need an exact and computationally expensive ab initio dynamical matrix to calculate phonon modes, the dynamical matrix may be calculated from bond hardness coefficients while setting atomic masses to unity. The soft-mode mutation operator includes calculating the dynamical matrix according to Equation (6):

$$D_{\alpha\beta}(a,b) = \sum_m \frac{\partial^2}{\partial \alpha_a^0 \partial \beta_b^m} \left( \frac{1}{2} \sum_{i,j,l,n} H_{i,j}^{l,n} \left( r_{i,j}^{l,n} - r_{0i,j}^{l,n} \right)^2 \right), \qquad (6)$$

with coefficients $\alpha$, $\beta$ denoting coordinates (x,y,z); coefficients a, b, i, j describing an atom in a unit cell; and coefficients l, m, n describing a unit cell number. $r_{i,j}^{l,n}$ is a distance between atom i in the unit cell l and atom j in the unit cell n, while is $r_{0i,j}^{l,n}$ is the corresponding bond distance. $H_{i,j}^{l,n}$ is a bond hardness coefficient between the atom i in the unit cell l and atom j in the unit cell n. For example, atoms are preferably treated as point particles and bonds as springs that connect the atoms with a stiffness determined by $H_{i,j}^{l,n}$. Bonds with a valence strength greater than input parameter goodBonds are included in $H_{i,j}^{l,n}$. Eigenvectors of $D_{\alpha\beta}(a,b)$ correspond to lowest non-zero eigenvalues and determine a direction of the soft mode mutation operator.

Valence strength is a chemical property of the bond between two atoms. A higher valence strength indicates a stronger bond between atoms. The input parameter goodbonds sets a threshold that determines which bonds are considered sufficiently strong to participate in the dynamical matrix. The dynamical matrix, as explained above, is used to calculate the eigenvectors and eigenvalues. The eigenvalue together with corresponding eigenvector is referred to as a mode. A mode having a relatively small eigenvalue is considered a soft mode in which mutation consists of movement of atoms along the eigenvector.

In step 145 of FIG. 1, the child group of crystal structures that are output from step 135 are added to the optimal group of crystal structures and a next generation is output in step 155. If in step 145 the output next generation is optimal, the method ends at step 160. Otherwise the method returns to step 115. Following output of the next generation of crystal structures, the above-described steps are repeated a predetermined number of times for a predetermined number of generations, to output an optimized crystal structure, preferably in Vienna Ab initio Simulation Package (VASP) format describing the crystal structure in terms of unit cell distances to provide dimensions for each atom in the unit cell in each direction and providing coordinates of each atom within the unit cell.

According to an aspect of the present invention, a user may implement halting criteria to stop the evolutionary algorithm after the predetermined number of generations is achieved. Specifically, the user may implement the halting criteria to stop the evolutionary algorithm when the next generation crystal structures output from at step 145 attain the ground state for the crystal structure and free energy does not decrease with another repetition.

According to an aspect of the present invention, the method includes removing chemistry-preserving constraints on the variation operator in step 135. Specifically, the chemistry-preserving constraints on the variation operator require input of a set of individual atoms. By removing the chemistry-preserving constraints, molecules may be inputted without specifying stoichiometry. For example, inputting the set of atoms with chemistry-preserving constraints in place for sodium (Na), chlorine (Cl) and oxygen (O) may be inputted according to a formula of: xNa+yCl+zO, where x, y, and z are integers. However, with the chemistry-preserving constraints removed, a molecule including Na, Cl and O may be inputted according to a formula: xNaCl+yNaO. Thus, with chemistry-preserving constraints in place, only one chemical structure is studied. However, when studying NaCl, without the chemistry-preserving constraints, all possible chemical compositions formed by Na and Cl, such as pure Na, pure Cl, NaCl, $Na_2Cl$, $NaCl_5$ etc., are inputted.

According to an aspect of the present invention, the method includes introducing a chemical transmutation operator in step 135. The chemical transmutation operator changes the identities of atoms in the structure, thus changing the crystal structure chemical composition. For example, where a hypothetical crystal structures is a mixture of elements A and B having a general formula $A_xB_y$, where x and y and non-negative integers, the chemical transmutation operator picks a random atom A and puts a random atom B in atom A's position. The chemical transmutation operator allows the user to change the chemical structure of the crystal structures and thus study a more diverse population of the chemical structures The method also includes determining the fitness function of the chemical structure as a difference between free energy per atom of the chemical structure and free energy per atom of all possible decompositions of the chemical structure according to known values of free energy. As described above, the fitness function of each crystal structure may be evaluated at step 120 of FIG. 1 by the free energy of a crystal structure. Alternatively, the crystal structure may be evaluated by comparison to the predetermined structure, or the free energy of the predetermined structure may have been previously calculated and saved in a history of a computer system running the evolutionary algorithm.

The embodiments described above provide a cumulative effect resulting in a method outperforming conventional methods. Other methods may successfully predict crystal structures with 15-40 atoms. However, aspects of the present invention successfully predict crystal structures with up to 160 atoms in the unit cell. Optimizing properties of a crystal structure and varying the crystal structure's stoichiometry provides steps forward to a fully computational material design.

Another aspect of the invention provides a method for predicting an optimized surface structure by inputting characterization information of a chemical structure and input parameters, with the characterization information including a number of atoms, a surface energy and a volume of a unit cell. A first convex hull of a first generation of surface structures is generated from the characterization information using a docking algorithm. Surface structures of the first generation of surface structures include a bulk substrate layer, an adatom layer and a vacuum layer. The first generation of surface structures is restricted based on a convex hull algorithm according to a user-defined chemical potential constraint.

The docking algorithm includes scanning the adatom layer for vacant sites and adding atoms to the vacant sites within the adatom layer based on predetermined conditions that include a coordination number and a distance from adjacent atoms. The docking algorithm includes outputting a configuration of the atoms added to the vacant sites.

The method includes outputting a second convex hull of the first generation of surface structures and optimizing the second convex hull of the first generation of surface structures according to the input parameters. The optimized second convex hull is input into a niching algorithm to select an optimal group of surface structures and a parent group of surface structures based on a fitness function. A child group of surface structures is produced from the parent group of surface structures by applying a variation operator to the adatom layer of the surface structures of the first generation of surface structures. The child group of surface structures is added to the optimal group of surface structures to form a second generation of surface structures. The optimizing through adding steps are repeated for a predetermined number of generations, surface structures having a chemical potential above a user-defined threshold are discarded.

An example of an application of an aspect of the present invention is provided using characterization information of the chemical structure of thirteen atoms per unit cell, an atomic number of 42 for each atom (molybdenum), good-bonds input parameter set to 0.7, to include bonds with valence strength above 0.7 in the calculation of dynamical Equation (5) above. With the fitness function set to optimize enthalpy, the first generation of crystal structures and subsequent generations of crystal structures are set to include five crystal structures, and the optimal group of crystal structures is set to include the two crystal structures with the lowest enthalpy to survive in the next generation.

The niching algorithm is set to select 80% of the optimized first generation of crystal structures to be the parent group of crystal structures and 20% of the optimized first generation of crystal structures to be the optimal group of crystal structures. The variation operators are set to produce a child group of crystal structures from the parent group of crystal structures according to proportions of 40% produced through the spatial heredity operator, 20% randomly produced according to a user-defined space group, and 40% produced by the soft-mode mutation operator. The user-defined space group in this example is set to a space group of one, which is a no symmetry group to demonstrate that a symmetrical crystal structure is obtained from non-symmetrical crystal structures.

A distance of 0.003 is set for an input parameter to indicate that a distance between crystal structures of less than 0.003 the crystal structures is considered identical, to discard duplicate crystal structures when selecting the parent group of crystal structures. Another input parameter is set to a distance of 0.030 to indicate that structures having a distance less than 0.030 are identical when selecting the optimal group of crystal structures using the niching algorithm. Accordingly, with respect to the current example, the degree of similarity between the fingerprint functions of each of the crystal structures calculated according to Equation (2).

For a garnet pyrope ($Mg_{24}Al_{16}Si_{24}O_{96}$) with 160 atoms in the cubic unit cell, a previous algorithm version could not find the ground state. However, an aspect of the present invention provides an algorithm that readily finds the ground state. In an embodiment, 64 fixed-cell calculations (30 structures/generation, with a maximum of 100 generations) were performed with a 100% success rate. An example of the calculations, in which ground state was found in the sixth, is provided in FIG. 4, which used methodological developments-symmetric initialization, antiseeds, cell splitting and softmutation.

Figure 4:
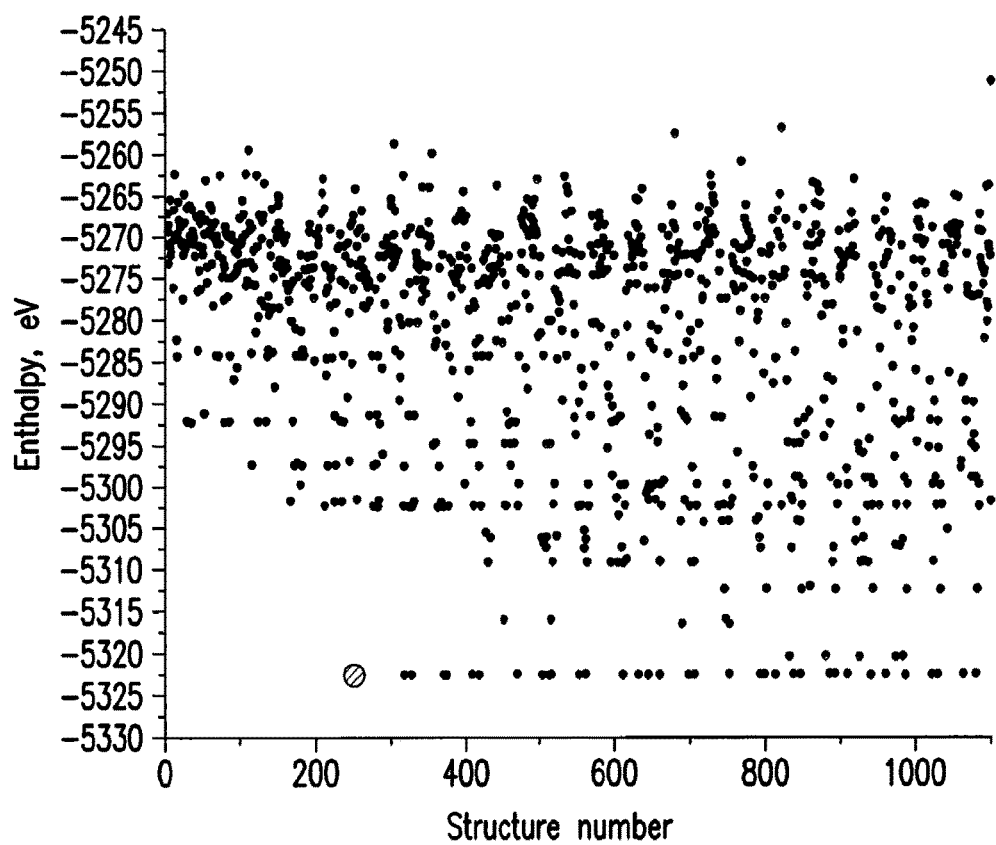
FIG. 4 is a graph illustrating optimized crystal structure predictions, according to an aspect of the present invention with one hundred and sixty atoms per cell in a fixed cubic cell, according to an aspect of the present invention.

FIG. 4 is a graph illustrating optimized crystal structure predictions, according to an aspect of the present invention with 160 atoms per cell in a fixed cubic cell. The example calculation provided in FIG. 4 is for pyrope ($Mg_3Al_2(SiO_4)_3$) with 160 atoms/cell in a fixed cubic cell. FIG. 4 clearly shows rapid improvement of the population quality in the first generations. FIG. 4 also shows that even after the ground state was found, a continued improvement of general quality of the population and finding new very low-energy structures is obtained.

Figure 5:
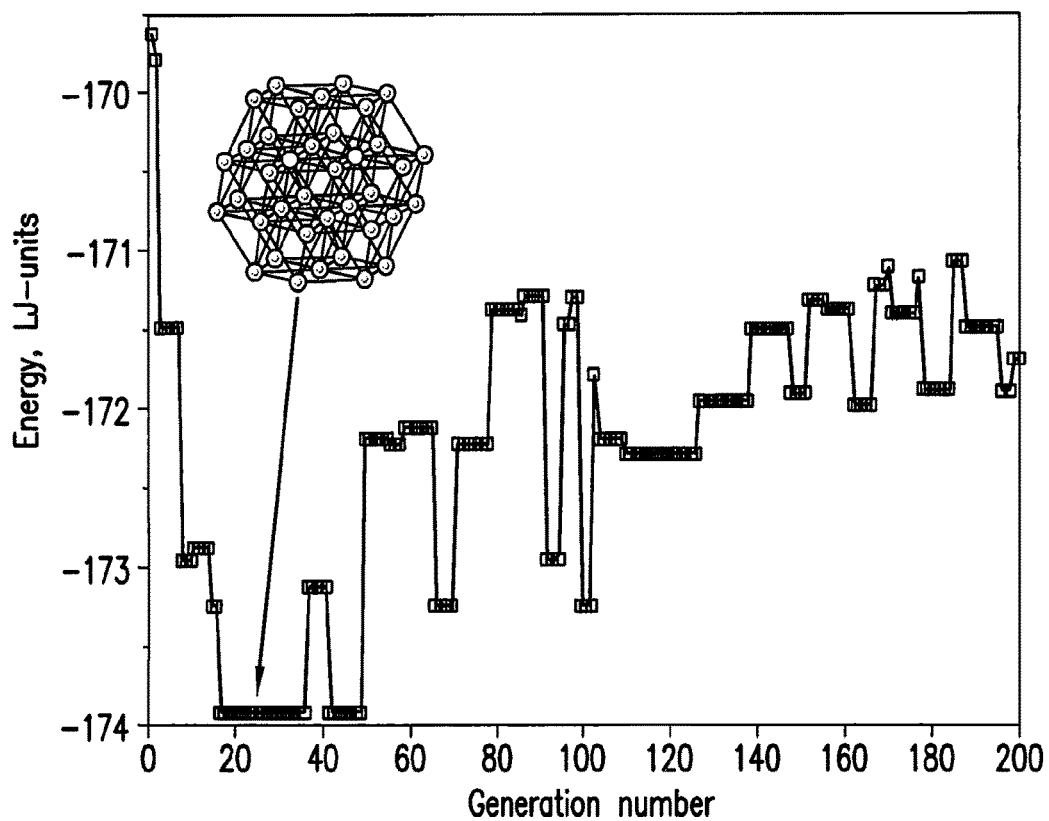
FIG. 5 is a graph providing an example of a calculation performed using antiseeds, according to an aspect of the present invention.

FIG. 5 is a graph providing an example of a calculation performed using antiseeds, according to an aspect of the present invention. FIG. The example calculation provided in FIG. 5 is a calculation of $LJ_{38}$ using antiseeds. In FIG. 5, energy of a best structure in each generation is plotted, showing that the algorithm, when antiseeds are used, does not get stuck on any candidate minima, and quickly finds the ground state.

In a preferred aspect, a system for predicting an optimized crystal structure using an evolutionary algorithm includes a processor configured to execute the above described method. Specifically, the methods of the present invention are implemented in systems that use software run on a computer processor to carry out the above described methods. While in preferred embodiments, the methods are carried out in an automated format, entirely within the computer processor, it should be understood that one or more components may be carried out by a human and that the methods may involve human interaction or intervention at one or more points.

The computer processor for conducting aspects of the methods of the present invention may be housed in devices that include desktop computers, scientific instruments, handheld devices, personal digital assistants, phones, a non-transitory computer readable medium, and the like. The methods need not be carried out on a single processor. For example, one or more steps may be conducted on a first processor, while other steps are conducted on a second processor. The processors may be located in the same physical space or may be located distantly. In some such embodiments, multiple processors are linked over an electronic communications network, such as the Internet. Preferred embodiments include processors associated with a display device for showing the results of the methods to a user or users, outputting results as a video image of a predicted crystal structure that include coordinates of atoms, molecules or motifs. The processors may be directly or indirectly associated with information databases, which include crystal structure databases. As used herein, the terms processor, central processing unit, and CPU are used interchangeably and refer to a device that is able to read a program from a computer memory, e.g., ROM or other computer memory, and perform a set of steps according to the program. The terms computer memory and computer memory device refer to any storage media readable by a computer processor. Examples of computer memory include, but are not limited to, RAM, ROM, computer chips, digital video discs, compact discs, hard disk drives and magnetic tape. Also, computer readable medium refers to any device or system for storing and providing information, e.g., data and instructions, to a computer processor, DVDs, CDs, hard disk drives, magnetic tape and servers for streaming media over networks. As used herein, encode refers to the process of converting one type of information or signal into a different type of information or signal to, for example, facilitate the transmission and/or interpretability of the information or signal. For example, image files can be converted into, i.e., encoded into, electrical or digital information.

While the invention has been shown and described with reference to certain aspects thereof, it will be understood by those skilled in the art that various changes in form and details may be made therein without departing from the spirit and scope of the present invention as defined by the appended claims and equivalents thereof.

What is claimed is:

1. A method for predicting an optimized crystal structure using an evolutionary algorithm in which characterization information of a chemical structure and input parameters are input, a first generation of crystal structures is generated from the characterization information using symmetrical initialization, the chemical structure of the first generation of crystal structures is optimized according to the input parameters, the crystal structures of the optimized first generation are input into a niching algorithm to select an optimal group of crystal structures and a parent group of crystal structures based on a fitness function, a child group of crystal structures is produced from the parent group of crystal structures using a variation operator, and the child group of crystal structures is added to the optimal group of crystal structures to form a next generation of crystal structures;

characterized in that an antiseed is created for population diversity, wherein every structure produced by the evolutionary algorithm is stored together with a width and a height of a Gaussian parameter as the antiseed.

2. The method of claim 1, wherein the fitness function of a structure i is modified using:

$$f_i = f_{i0} + \sum_a W_a \exp\left(-\frac{D_{ia}^2}{2\sigma_a^2}\right),$$

where $f_{i0}$ is an initial fitness function, a summation is performed over each stored antiseed having height $W_a$ and width $\sigma_a$, $D_{ia}$ is a distance between a current structure and an antiseed structure in a fingerprint metric space, $\sigma_a$ is proportional to an average cosine distance between fingerprints of all pairs of structures in a population, and $W_a$ is proportional to a fitness variance.

3. The method of claim 2, wherein the modified fitness function of the structure i places additional evolutionary pressure on previously sampled structures.

4. The method of claim 1, wherein the symmetrical initialization comprises:

splitting a unit cell having the input chemical structure;
selecting a space group compatible with the unit cell;
configuring a symmetrical initialization unit cell according to the selected space group and a predetermined volume of the unit cell;
locating a plurality of atoms of the symmetrical initialization unit cell at a plurality of positions;
multiplying coordinates of each of the plurality of atoms by space group symmetry operations;

merging the plurality of atoms to a new position by averaging of coordinates when an inter-atomic distance between the plurality of atoms is determined to be within a user-defined threshold to produce a merged atom; and discarding the merged atom when the merged atom is determined to be incompatible with the space group symmetry operation.

5. The method of claim 1, wherein the niching algorithm further comprises:

calculating a set of fitness functions and a fingerprint function for each crystal structure of the first generation of crystal structures;

determining a degree of similarity between the fingerprint function;

determining a value of the fitness function for each crystal structure of the first generation of crystal structures from the set of fitness functions;

selecting the optimal group of crystal structures according to the value of the fitness function and the degree of similarity;

selecting the parent group of crystal structures according to the value of the fitness function; and discarding a first parent crystal structure from the parent group of crystal structures when a distance between the fingerprint function of the first parent crystal structure and the fingerprint function of a second parent crystal structure is smaller than a user-defined threshold.

6. The method of claim 1, further comprising:
removing chemistry-preserving constraints on the variation operator;
introducing a chemical transmutation operator; and
determining the fitness function of the chemical structure as a minimal difference between free energy per atom of the chemical structure and free energy per atom of each decomposition of the chemical structure.

7. The method of claim 1, wherein the variation operator includes a local order element determined by:

$$\prod_i = \sqrt{\sum_B \frac{N_B}{N} \frac{\Delta}{(V/N)^{1/3}} |F_{A_iB}|^2} \,,$$

wherein $\Pi_i$ is the local order element for atom i, N is a total number of atoms in the unit cell, V is a unit cell volume, $FP_{A_iB}$ is a fingerprint vector of an atom $A_i$, and B represents each atom type present in the unit cell.

8. The method of claim 1, wherein the fitness function includes variables of at least one of free energy, density, hardness, dielectric constant and bandgap.

9. A system for predicting an optimized crystal structure using an evolutionary algorithm, comprising a processor configured to execute the method of claim 1.

* * * * *